(12) United States Patent
Moran et al.

(10) Patent No.: US 8,415,316 B2
(45) Date of Patent: Apr. 9, 2013

(54) METHOD FOR INCREASING BONE MASS

(75) Inventors: Elizabeth Moran, Yardley, PA (US); Stephen Flowers, Hamilton, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 218 days.

(21) Appl. No.: 12/851,610

(22) Filed: Aug. 6, 2010

(65) Prior Publication Data

US 2011/0033443 A1    Feb. 10, 2011

Related U.S. Application Data

(60) Provisional application No. 61/273,717, filed on Aug. 6, 2009.

(51) Int. Cl.
*C12N 15/11* (2006.01)
*A61K 48/00* (2006.01)
*C07H 21/02* (2006.01)
*C07H 21/04* (2006.01)

(52) U.S. Cl. .................................. 514/44 A; 536/24.5

(58) Field of Classification Search .................. 514/44
See application file for complete search history.

(56) References Cited

PUBLICATIONS

Ramirez-Carrozzi et al. (Genes and Development, 2006 vol. 20:282-296).*
Qi Shen (Dissertation Abstract, Mar. 2, 2006).*
Liu et al. (Genes and Development, 2004 vol. 18:673-686).*
de la Serna et al. "Chromatin Remodelling in Mammalian Differentiation: Lessons From ATP-Dependent Remodellers" Nature Reviews Genetics 2006 vol. 7 (6): 461-473.

(Continued)

*Primary Examiner* — Terra Cotta Gibbs
(74) *Attorney, Agent, or Firm* — Licata & Tyrrell P.C.

(57) ABSTRACT

The present invention features methods for promoting the differentiation of osteoblast bone forming cells to a mineralization phenotype and increasing bone mass using inhibitors of Brahma. Subjects benefiting from such treatment may have non-union fractures, osteopenia or osteoporosis, osteosarcoma, or a bone graft or bone fusion or orthopedic and dental implants, osteolytic bone disease, skeletal defects or deficiencies or periodontal disease.

12 Claims, 1 Drawing Sheet

PUBLICATIONS

Griffin et al. "The Chromatin-Remodeling Enzyme BRG1 Plays an Essential Role in Primitive Erythropoiesis and Vascular Development" Development 2008 vol. 135: 493-500.

Kingston, R. E. and Narlikar, G. J. "ATP-Dependent Remodeling and Acetylation as Regulators of Chromatin Fluidity" Genes & Development 1999 vol. 13: 2339-2352.

Klochendler-Yeivin et al. "SWI/SNF Chromatin Remodeling and Cancer" Current Opinion in Genetics & Development 2002 vol. 12: 73-79.

Lee et al. "Histone Deacetylase 1-Mediated Histone Modification Regulates Osteoblast Differentiation" Molecular Endocrinology 2006 vol. 20: 2432-2443.

Liu et al. "TopBP1 Recruits Brg1/Brm to Repress E2F1-Induced Apoptosis, a Novel pRb-Independent and E2F1-Specific Control for Cell Survival" Genes and Development 2004 vol. 18: 673-686.

Mohrmann, L. and Verrijzer, C. P. "Composition and Functional Specificity of SWI2/SNF2 Class Chromatin Remodeling Complexes" Biochimica et Biophysica Acta 2005 vol. 1681: 59-73.

Montecino et al. "Nucleosome Organization and Targeting of SWI/SNF Chromatin-Remodeling Complexes: Contributions of the DNA Sequence" Biochemistry and Cell Biology 2007 vol. 85: 419-425.

Reyes et al. "Altered Control of Cellular Proliferation in the Absence of Mammalian Brahma (SNF2α)" The EMBO Journal 1998 vol. 17 (23): 6979-6991.

Roberts, C. W. M. and Orkin, S. H. "The SWI/SNF Complex—Chromatin and Cancer" Nature Reviews Cancer 2004 vol. 4: 133-142.

Smith, C. L. and Peterson, C. L. "ATP-Dependent Chromatin Remodeling" Current Topics in Developmental Biology 2005 vol. 65: 115-148.

Strobeck et al. "Compensation of BRG-1 Function by Brm" The Journal of Biological Chemistry 2002 vol. 277 (7): 4782-4789.

Vignali et al. "ATP-Dependent Chromatin-Remodeling Complexes" Molecular and Cellular Biology 2000 vol. 20 (6): 1899-1910.

Villagra et al. "Chromatin Remodeling and Transcriptional Activity of the Bone-Specific Osteocalcin Gene Require CCAAT/Enhancer-Binding Protein β-Dependent Recruitment of SWI/SNF Activity" The Journal of Biological Chemistry 2006 vol. 281 (32): 22695-22706.

* cited by examiner

DAY 0 – PROMOTER REPRESSED

DAY 7 – PROMOTER IN TRANSITION

DAY 14/21 – PROMOTER ACTIVE

```
                        SEQUENCE LISTING

<160> NUMBER OF SEQ ID NOS: 21

<210> SEQ ID NO 1
<211> LENGTH: 64
<212> TYPE: DNA
<213> ORGANISM: Artificial sequence
<220> FEATURE:
<223> OTHER INFORMATION: Synthetic oligonucleotide

<400> SEQUENCE: 1
gatccccgat ccagaagctc tccaaattca agagatttgg agagcttctg gatcttttttg      60 gaaa                                                                    64

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
gtcataagcc tgaggcaaa                                                    19

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 3
gcctatggag tccatgcac                                                    19

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
ggctgggaca gacagaatgt                                                   20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
ctttgtccct cgatggttgt                                                   20
```

```
<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
gcaaggtttt tggagatgga                                              20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
gcactttggg aatgaaagga                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
tgtgagttgt tgggccacta                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
tctggctgaa ttgcaagttg                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
acaggtggtc agcgcttagt                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
atgtgggtac tgggagcaag                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
```
caggtgtggt ggcctaaagt                                            20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
aactgcctga ggtgctgagt                                            20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
acttgttccc gtacccacag                                            20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
ttctgtcccc tttccctctt                                            20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
cctgagtttg gggtgaaatg                                            20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tgacaccaga cctcagcaag                                            20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
agcctacagg ctggcttaca                                            20

<210> SEQ ID NO 19
<211> LENGTH: 20
<212> TYPE: DNA
<213> ORGANISM: Artificial sequence -continued

```
<220> FEATURE:
<223> OTHER INFORMATION: Synthetic oligonucleotide

<400> SEQUENCE: 19
ctacccgtgc tatggacgat                                              20

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 20
ctgaactggg caaatgagga ca                                           22

<210> SEQ ID NO 21
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 21
aggggatgct gccaggacta at                                           22
```

METHOD FOR INCREASING BONE MASS

INTRODUCTION

This application claims benefit of priority to U.S. Provisional Application Ser. No. 61/273,717, filed Aug. 6, 2009, the content of which is incorporated herein by reference in its entirety.

This invention was made with government support under contract number GM073257 awarded by the National Institutes of Health. The government has certain rights in the invention.

BACKGROUND OF THE INVENTION

The mammalian SWI/SNF (SWItch/Sucrose NonFermenting) complex is an evolutionarily well-conserved ATPase-powered chromatin-remodeling assembly composed of approximately 10 subunits. This complex (also known as the BRG1-associated factors (BAF) complex) coordinates the disruption of nucleosomes to permit the binding of various transcription factors, an activity crucial for proper differentiation and development (Kingston & Narlikar (1999) *Genes Dev.* 13:2339-2352; Vignali, et al. (2000) *Mol. Cell. Biol.* 20:1899-1910; Mohrmann & Verrizer (2005) *Biochim. Biophys. Acta.* 1681:59-73; Smith & Peterson (2005) *Curr. Top. Dev. Biol.* 65:115-148; de la Serna, et al. (2006) *Nat. Rev. Genet.* 6:461-473).

The entity known as the mammalian SWI/SNF complex is composed of a small series of compositionally distinct assemblies distinguished by the presence of alternative subunits. The choice of ARID (AT-rich interaction domain) family subunit (ARID1A or ARID1B) is a determinant of complexes with generally opposing roles in cell cycle control (Nagl, et al. (2007) *EMBO J.* 26:752-763; Blais & Dynlacht (2007) *Curr. Opin. Cell Biol.* 19:658-662). The complexes also contain either of two closely related alternative ATPases: human Brahma (BRM; Mohrmann & Verrijzer (2005) supra) or Brahma-related gene 1 (BRG1). Although BRM and BRG1 share a high degree of amino acid sequence identity, they are not equally important for development. Brg1-null mice die at a pre- or peri-implantation stage (Bultman, et al. (2000) *Mol. Cell.* 6:1287-1295), indicating a critical developmental role for BRG1. In contrast, Brm-null mice are viable and fertile, exhibiting only mild abnormalities that include a larger animal size and deregulated cell growth control in derived fibroblasts (Reyes, et al. (1998) *EMBO J.* 17:6979-6991). This study also showed an increased level of BRG1 in the animal tissues in the absence of BRM, and several studies indicate that BRG1- and BRM-containing SWI/SNF complexes play largely compensatory roles in cell cycle control (Strobeck, et al. (2002) *J. Biol. Chem.* 277:4782-4789; Klochendler-Yeivin, et al. (2002) *Curr. Opin. Genet. Dev.* 12:73-79; Roberts & Orkin (2004) *Nat. Rev. Cancer.* 4:133-142). Due to these phenotypes, it has been generally thought that BRM plays a similar but mostly auxiliary role to BRG1 in regulation of tissue-specific gene expression (de la Serna, et al. (2006) supra). However, few studies have compared the roles of BRM and BRG1 directly in differentiation models, and where considered (Griffin, et al. (2008) *Development (Camb.)* 135:493-500), BRM was generally confirmed as non-essential with relatively little other detail.

SUMMARY OF THE INVENTION

The present invention features a method for promoting the differentiation of osteoblast bone forming cells or progenitor cells thereof to a mineralization phenotype by contacting osteoblast bone forming cells or progenitor cells thereof with an effective amount of an inhibitor of BRM. In one embodiment, the inhibitor attenuates expression of BRM. In another embodiment, the inhibitor attenuates the activity of BRM.

The present invention also features a method for increasing bone mass, bone healing or bone formation by administering to a subject in need of osteoinduction an effective amount of an inhibitor of BRM. In one embodiment, the inhibitor attenuates expression of BRM. In another embodiment, the inhibitor attenuates BRM activity. Subjects benefiting from such treatment may have a non-union fracture, osteopenia or osteoporosis, osteosarcoma, a bone graft, a bone fusion or arthrodesis procedure, a skeletal defect or deficiency, osteoarthritis, a periodontal disease or defect, an osteolytic bone disease or a post-orthopedic implantation or post-dental implantation.

DETAILED DESCRIPTION OF THE INVENTION

Figure 1:
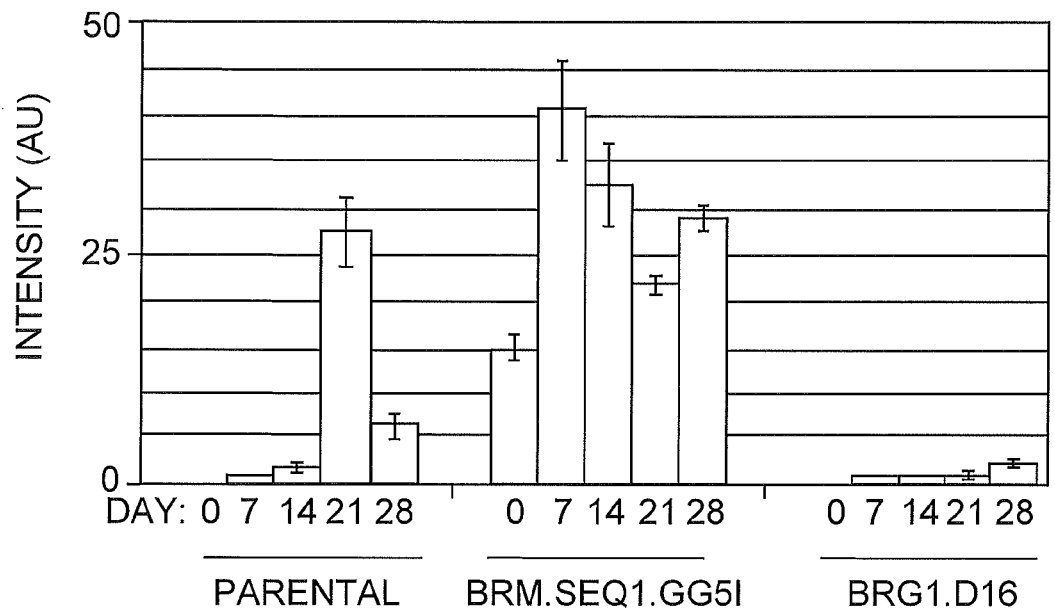
FIG. 1 shows the regulation of osteocalcin expression in BRM- and BRG1-depleted lines. Parental and knockdown lines were cultured in differentiation medium; total RNA was isolated at days 0, 7, 14, 21, and 28, as indicated, and analyzed by northern blot with sequentially applied probes for osteocalcin (OSC) and glyceraldehyde-3-phosphate dehydrogenase (GAPDH). Northern blot analysis from three independent experiments was quantified by phosphoimaging, normalized to glyceraldehyde-3-phosphate dehydrogenase signals, averaged, and plotted as arbitrary units (AU) of phosphoimaging values. Error bars indicate the average deviation from the mean.

It has now been found that inhibition of BRM accelerates the differentiation of osteoblast bone forming cells to a mineralization phenotype. The roles of BRG1 and BRM in differentiation were analyzed by shRNA-mediated depletion in a differentiation model chosen for its well-ordered multistep nature. Osteoblast precursors including the mouse calvaria-derived MC3T3-E1 line undergo a tightly regulated differentiation process when induced with appropriate agents such as ascorbic acid and a source of organic phosphate (Quarles, et al. (1992) *J. Bone Miner. Res.* 7:683-692; Franceschi, et al. (1994) *J. Bone Miner Res.* 9:843-854; Choi, et al. (1996) *J. Cell. Biochem.* 61:609-618; Stein, et al. (1996) *Physiol. Rev.* 76:593-629; Beck, et al. (2001) supra). An important advantage of this model is that differentiation proceeds through discreet stages with predictable timing, providing a window for observing subtle changes in the rate of differentiation in addition to overall inhibition of differentiation. The expectation was that BRG1 depletion would block differentiation, whereas BRM depletion might cause modest delay. However, the studies described herein unexpectedly revealed a programmatic role for BRG1-containing complexes in repression of BRG1-dependent differentiation. Deficiency of BRM did not correlate with impaired differentiation; in contrast, it resulted in an accelerated rate of mineralization with constitutively higher levels of expression of osteogenic markers. These results reveal a new aspect of the alternative BRM and BRG ATPases, identifying them as determinants of SWI/SNF complexes with opposing roles across a whole program of tissue-specific gene expression. Furthermore, the results described herein indicate that at least one mechanism by which BRM-containing complexes effect repression is by mediating promoter association of the histone deacetylase, HDAC1. This interpretation is supported by analysis elsewhere of the effects of HDAC1 depletion in a rat osteosarcoma cell model, wherein depletion of HDAC1 via small interfering RNA-mediated knockdown was accompanied by increased alkaline phosphatase activity and heightened expression of osteoblast differentiation markers (Lee, et al. (2006) *Mol. Endocrinol.* 20:2432-2443), a phenotype very similar to the phenotype reported here for BRM-depleted cells. These factors may not be the only ones active at the promoter, but the present results establish that BRM-containing complexes are essential for repression and that the default condition of the osteocalcin promoter in the absence of a BRM complex is active expression, even without a signal for differentiation.

Accordingly, the present invention pertains to antagonizing the activity of BRM or inhibiting the expression of BRM to promote, stimulate or accelerate the differentiation of osteoblast bone forming cells or progenitors thereof to a mineralization phenotype with elevated levels of expression of osteogenic markers. In this respect, the invention encompasses methods of treating or mitigating diseases or conditions characterized by bone loss or bone deficiency, including osteopenia and osteoporosis, by increasing bone mass; promoting healing of non-union fractures; and enhancing healing and patency of orthopedic and dental implants, bone allografts and bone fusions; treatment of osteolytic bone disease, skeletal defects or deficiencies or periodontal disease using BRM inhibitors.

The target cells of this invention include osteoblast bone forming cells or progenitor cells thereof. As is known in the art, an osteoblast bone forming cell is a cell from which bone develops. These cells secrete osteoid, which forms the bone matrix. In context of the present invention, a progenitor cell of an osteoblast is a mesenchymal stem cell.

As used herein, an inhibitor of BRM or BRM inhibitor is an agent that either attenuates or inhibits the expression (e.g., transcription or translation) or attenuates or inhibits the activity of BRM. Inhibitory agents can be any class of compound including small organic molecules, peptides, proteins, nucleic acids, carbohydrates and the like. For example, agents that inhibit the activity of BRM include, but are not limited to, antagonistic antibodies or antibody fragments specific for BRM, dominant-negative mutants of BRM (Liu, et al. (2004) *Genes Dev.* 18:673-686), and molecules routinely used in the art to inhibit ATP-dependent helicases. In particular embodiments, the inhibitor interferes with the intrinsic enzyme activity of BRM, the intrinsic protein-protein interactions of BRM and/or the binding of BRM-containing protein complex to DNA.

In particular embodiments, the inhibitor of BRM is an agent that inhibits or attenuates the expression of BRM. As used herein, the phrase "attenuates BRM expression" means administering or expressing a BRM inhibitor to specifically reduce transcription of the BRM mRNA or translation of the BRM mRNA into protein, either through mRNA cleavage or through direct inhibition of translation. The reduction in expression of the BRM mRNA or the corresponding protein is commonly referred to as "knock-down" and is reported relative to levels present following administration or expression of a non-targeting control molecule (e.g., a non-targeting control siRNA). Knock-down of expression of an amount including and between 50% and 100% is contemplated by embodiments herein. However, it is not necessary that such knock-down levels be achieved for purposes of the present invention. Knock-down is commonly assessed by measuring the mRNA levels using quantitative polymerase chain reaction (qPCR) amplification or by measuring protein levels by western blot or enzyme-linked immunosorbent assay (ELISA). Further techniques for measuring knock-down include RNA solution hybridization, nuclease protection, northern hybridization, gene expression monitoring with a microarray, antibody binding, radioimmunoassay, and fluorescence activated cell analysis.

BRM inhibitors that inhibit BRM expression can be small molecule inhibitors or nucleic acids that block BRM expression. Nucleic acids of use in this invention include antisense molecules, ribozymes, RNAi, and triple helix molecules that specifically modulate the expression of BRM without modulating the expression of other proteins such as BRG1. Antisense molecules and ribozymes are well-known to those of skill in the art. See, e.g., Crooke & Lebleu, eds., *Antisense Research and Applications* (1993) CRC Press; and *Antisense RNA and DNA* (1988) Melton, Ed., Cold Spring Harbor Laboratory Cold Spring Harbor, N.Y. Antisense RNA and DNA molecules act to directly block the translation of mRNA by binding to targeted mRNA and preventing protein translation. An example of an antisense polynucleotide is an oligodeoxyribonucleotide derived from the translation initiation site, e.g., between −10 and +10 regions of the relevant nucleotide sequence.

Although antisense sequences may be directed against the full-length genomic or cDNA of BRM, they also can be shorter fragments or oligonucleotides, e.g., polynucleotides of 100 or less bases. Although shorter oligomers (8-20) are easier to prepare and are more permeable in vivo, other factors also are involved in determining the specificity of base pairing. For example, the binding affinity and sequence specificity of an oligonucleotide to its complementary target increases with increasing length. It is contemplated that oligonucleotides of 8, 9, 10, 11, 12, 13, 14, 15, 16, 17, 18, 19, 20, 25, 30, 35, 40, 45, 50, or more base pairs will be used.

Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead and other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the target gene containing the cleavage site can be evaluated for predicted structural features, such as secondary structure, that may render the oligonucleotide sequence unsuitable. The suitability of candidate targets also can be evaluated by testing their accessibility to hybridization with complementary oligonucleotides, using ribonuclease protection assays. See, e.g., WO 93/2356; and U.S. Pat. No. 5,093,246.

Nucleic acid molecules used in triple helix formation for the inhibition of transcription generally are single stranded and composed of deoxyribonucleotides. The base composition is designed to promote triple helix formation via Hoogsteen base pairing rules, which generally require sizeable stretches of either purines or pyrimidines to be present on one strand of a duplex. Nucleotide sequences can be pyrimidine-based, which results in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules can be selected that are purine-rich, for example, containing a stretch of G residues. These molecules form a triple helix with a DNA duplex that is rich in GC pairs, wherein the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Another technique of particular use in reducing the expression of a gene is RNA interference (RNAi). RNAi allows for the selective knockout of a target gene in a highly effective and specific manner. This technique involves introducing into a cell an RNAi molecule having a sequence corresponding to a portion of the target gene. The RNAi molecule causes a rapid destruction of the target gene's mRNA. See, e.g., Hammond, et al. (2001) Nature Rev. Gen. 2:110-119; Sharp (2001) Genes Dev. 15:485-490. Methods and procedures for successful use of RNAi technology are well-known in the art, and have been described in, for example, Waterhouse, et al. (1998) Proc. Natl. Acad. Sci. USA 95(23):13959-13964.

RNAi molecules include, but are not limited to, double-stranded short interfering RNA (siRNA), short hairpin RNAs (shRNAs), single-stranded siRNAs, microRNAs (mRNAs), and dicer-substrate 27-mer duplexes. Unless otherwise noted, the term "siRNA" refers to a double-stranded interfering RNA. The length of an RNAi molecule is typically 19 to 49 nucleotides, and may be 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. More particularly, siRNAs are about 19 to 28 nucleotides, or 20 to 25 nucleotides, or 21 to 22 nucleotides in length and often contain 2-nucleotide 3' overhangs, and 5' phosphate and 3' hydroxyl termini. RNAi molecules of the invention can contain one or more chemically modified nucleotides, one or more deoxyribonucleotides, and/or one or more non-phosphodiester linkages and include a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA. Moreover, non-nucleotide material may be bound to the RNAi molecule, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, RNAis may include a purine nucleotide at the ends of overhangs. Conjugation of cholesterol to the 3' end of the sense strand of a siRNA molecule by means of a pyrrolidine linker, for example, also provides stability to a siRNA molecule. Further modifications include a 3' terminal biotin molecule, a peptide known to have cell-penetrating properties, a nanoparticle, a peptidomimetic, a fluorescent dye, or a dendrimer, for example.

The target sequence that binds the RNAi molecule can be selected experimentally or empirically. For example, empirical observations have indicated that shRNA oligonucleotides targeting the transcriptional start site of the target gene (Hannon (2002) Nature 418:244-51) or targeting the 3' untranslated region of the mRNA (He and Hannon (2004) Nature 5:522-531) are more effective at blocking gene expression. Further, siRNA target sites in a gene of interest are selected by identifying an AA dinucleotide sequence, typically in the coding region, and not near the start codon (within 75 bases) as these may be richer in regulatory protein binding sites which can interfere with binding of the siRNA (see, e.g., Elbashir, et al. (2001) Nature 411: 494-498). The subsequent 19-27 nucleotides 3' of the AA dinucleotide can be included in the target site and generally have a G/C content of 30-50%. In this respect, interfering RNA target sequences (e.g., siRNA target sequences) within a target mRNA sequence can be selected using available design tools. RNAi molecules corresponding to these target sequences are then tested by transfection of cells expressing the target mRNA followed by assessment of knockdown as described herein. Interfering RNAs that produce a knockdown in expression of between 50% and 100% are selected for further analysis.

RNAi can be prepared, for example, using chemically-synthesized RNA, e.g., solid phase phosphoramidite chemical synthesis. Alternatively, RNAi molecules can be expressed endogenously from plasmid or viral expression vectors or from minimal expression cassettes, for example, PCR generated fragments containing one or more promoters and an appropriate template or templates for the interfering RNA. Examples of commercially available plasmid-based expression vectors for shRNA include members of the pSilencer™ series (Ambion; Austin, Tex.) and pCpG-siRNA (InvivoGen; San Diego, Calif.). Viral vectors for expression of interfering RNA may be derived from a variety of viruses including adenovirus, adeno-associated virus, lentivirus (e.g., HIV, FIV, and EIAV), and herpes virus. See, Brummelkamp, et al. (2002) Science 296(5567):550-3; Lee, et al. (2002) Nat. Biotechnol. 20(5):500-5; Miyagashi & Taira (2002) Nat. Biotechnol. 20(5):497-500; Paddison, et al. (2002) Proc. Natl. Acad. Sci. USA 99(3):1443-8; Paul, et al. (2002); and Sui, et al. (2002) Proc. Natl. Acad. Sci. USA 99(8):5515-20. Examples of commercially available viral vectors for shRNA expression include pSilencer™ adeno (Ambion) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art.

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Web-based design and kits for production of dsRNA for use in RNAi are available commercially, e.g., from New England Biolabs Inc., Ambion Inc., Invitrogen, Dharmacon, Integrated DNA Technologies, Genscript, or Proligo web sites. Methods of transfection of dsRNA or plasmids engineered to make dsRNA are routine in the art. For example, given the efficacy of a VEGFR1 siRNA developed by Sirna Therapeutics (San Francisco, Calif.; Singerman (2009) *Retina* 29(6 Suppl):S49-50) for the treatment of age-related macular degeneration, one of skill in the art can appreciate dosing of such molecules for achieving the desired therapeutic result with no systemic or local adverse events.

Target sequences for antisense molecules, ribozymes, RNAi, and triple helix molecules can be derived from known nucleic acid sequences encoding BRM (also known as BAF190B, SNF2A, SNF2L2, and ATP-dependent helicase SMARCA2, SNF2-alpha). For example, the GENBANK database provides the sequence for human BRM under Accession Nos. P51531, NP_620614 or NP_003061. Equivalents of the above cited sequences are also encompassed by the invention and include alternative splice forms, allelic forms, isozymes, or a cognate thereof. A cognate is a BRM sequence from another mammalian species that is homologous to human BRM (i.e., an ortholog). BRM nucleic acid sequences related to human BRM include those having GENBANK Accession Nos. NP_001092585 (*Bos taurus*), NP_035546 (*Mus musculus*), NP_001004446 (*Rattus norvegicus*), and NP_990470 (*Gallus gallus*). Exemplary target sequences and RNAi molecules of use in the instant invention are disclosed in the Examples as SEQ ID NO:1 and SEQ ID NO:2.

Having demonstrated that inhibition of BRM accelerates differentiation of osteoblast bone forming cells to a mineralization phenotype with elevated levels of expression of osteogenic markers, the present invention features methods for increasing bone mass, bone formation and/or bone healing by administering to a subject (e.g., a human or other mammal) in need of osteoinduction an effective amount of an inhibitor of BRM. As used herein, osteoinduction refers to the stimulation of bone growth at a site within a subject at which little or no bone growth would occur if the site were left untreated. In this respect, use of a BRM inhibitor can result in a measurable increase in bone mass, bone healing or bone formation in a subject as compared to a subject not treated with a BRM inhibitor. Such an increase in bone mass, bone healing, or bone formation can be determined by conventional methods such as DXA (Dual Energy X-ray Absorptiometry), pDXA (Peripheral Dual Energy X-ray Absorptiometry), SXA (single Energy X-ray Absorptiometry), QUS (Quantitative Ultrasound), QCT (Quantitative Computed Tomography), pQCT (Peripheral Quantitative Computed Tomography), RA (Radiographic Absorptiometry), DPA (Dual Photon Absorptiometry), and SPA (Single Photon Absorptiometry).

Conventional technology for non-union fracture repair involves implantation of various growth factors to promote bone growth, including but not limited to BMP-4, BMP-2, IGF-1 and insulin. Some of these growth factors are proteins that are prohibitively expensive to produce. In addition, growth factors work cooperatively, so optimal therapy requires multiple factors. However, due to practical limitations, typical therapy is limited to a high dose of just one factor. Accordingly, one embodiment of the invention features the use of an inhibitor of BRM as an alternative or adjunct therapy in the treatment of non-union facture repair. Subjects benefiting from this treatment include those in need of treatment of non-union fractures, segmental gaps or bone voids caused, for example, by removal of a bone tumor or cyst, or other severe or massive bone trauma. In so far as bone growth normally occurs at bone injuries such as simple or hairline fractures and well-opposed complex fractures with minimal gaps without the need for further treatment, subjects with such injuries may or may not benefit from treatment with a BRM inhibitor.

Conventional treatment of osteopenia (i.e., a T-score of between −1 and −2.5) or osteoporosis (i.e., a T-score between 2.5 and −1) involves the use of bisphosphonates, inhibitors of osteoclasts, which are the cells responsible for bone breakdown. Similarly, osteosarcomas are conventionally treated with various anti-cancer cytotoxic drugs or resection. However, these treatment regimens do not result in osteoinduction. In this respect, other embodiments of the invention feature the use of an inhibitor of BRM as an alternative or adjunct therapy in the treatment of osteopenia, osteoporosis and osteosarcomas.

Furthermore, induced bone growth via BRM inhibition can be therapeutically beneficial at certain sites within a subject (referred to as "ectopic" sites) where bone tissue would not normally be found, such as a site in need of a bone graft, bone fusion or arthrodesis procedure. Fusions are commonly used to treat lower back pain by physically coupling one or more vertebrae to its neighbor. The bone created by such a fusion is located at a site not normally occupied by bone tissue. Osteoinduction at these ectopic sites can act as a "graft substitute" whereby induced bone growth between the vertebrae takes the place of a graft and obviates the need for a second operation to harvest bone for the grafting procedure.

Induction of bone formation is also needed for treating skeletal defects or deficiencies such as acquired and congenital craniofacial and other skeletal or dental anomalies (see e.g., Glowacki, et al. (1981) *Lancet* 1:959); performing dental and periodontal reconstructions where lost bone replacement or bone augmentation is required such as in a jaw bone; and supplementing alveolar bone loss resulting from periodontal disease to delay or prevent tooth loss (see, e.g., Sigurdsson, et al. (1995) *J. Periodontol.* 66:511). Moreover, the method of the invention additionally serves to provide (and retain) new bone needed to serve as an anchor for prostheses such as artificial hips, knees and shoulders.

In osteoarthritis, the cartilage between the bones wears away in the joints. As osteoarthritis gets worse, the cartilage disappears and bone rubs on bone. Bony spurs or growths usually form around the joint. In this respect, an inhibitor of BRM can be used as an alternative or adjunct therapy in the treatment osteoarthritis.

Osteolytic bone disease or osteolysis refers to an active resorption of bone matrix by osteoclasts as part of an ongoing disease process. While bone resorption is commonly associated with many diseases or joint problems, the term osteolysis generally refers to a problem common to artificial joint replacements such as total hip replacements, total knee replacements and total shoulder replacements. There are several biological mechanisms which may lead to osteolysis. In total hip replacement the generally accepted explanation for osteolysis involves wear particles. As the body attempts to clean up these wear particles it triggers an autoimmune reaction which causes resorption of living bone tissue. Osteolysis is usually progressive and requires a revision surgery. Therefore, a BRM inhibitor described herein can be used as an alternative or adjunct therapy in the treatment osteolysis.

Inhibitors of BRM can be delivered directly to the site in need of osteoinduction by tissue injection; by direct application with a placement device (e.g., ceramics, calcium phosphates, or other synthetic materials which have similar biomechanical properties to bone); or by a slow release device implanted adjacent to site in need of osteoinduction. Systemic or parenteral administration is also contemplated including but not limited to intravenous, subcutaneous, and oral delivery.

For administration to a human or mammalian subject, one or more inhibitors of BRM can be mixed with an appropriate physiologically acceptable carrier such as water, buffer, saline, glycine, hyaluronic acid, mannitol, and the like. Acceptable carriers for administration of a nucleic acid molecule for inhibiting expression of BRM include the cationic lipid-based transfection reagents TRANSIT-TKO (Mirus Corporation; Madison Wis.), LIPOFECTIN, LIPOFECTAMINE, OLIGOFECTAMINE (Invitrogen; Carlsbad, Calif.), or DHARMAFECT (Dharmacon; Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for osteoblast bone forming cells, for example. Further, the liposomes may be PEGylated liposomes.

Inhibitors of BRM may be delivered in solution, in suspension, emulsions or in bioerodible or non-bioerodible delivery devices. Moreover inhibitors can be delivered alone, as components of covalent conjugates, complexed with cationic lipids, cationic peptides, or cationic polymers, or encapsulated in targeted or non-targeted nanoparticles.

The dose required to achieve an effective concentration at the target cells (i.e., osteoblast bone forming cells or progenitor cells thereof) will vary depending on a number of factors including the delivery method, the site of delivery, the number of cell layers between the delivery site and the target cell or tissue, whether delivery is local or systemic, etc. Moreover, an effective amount of a formulation may depend on factors such as the age, race, and sex of the subject, the severity of the condition being treated, the rate of target gene transcript/protein turnover, RNAi potency, and RNAi stability, for example.

EXAMPLE 1

Materials and Methods

Materials and Cell Culture. Penicillin and streptomycin were purchased from Mediatech (Herndon, Va.). Ascorbic acid, β-glycerol phosphate, sodium phosphate mono and dibasic, Alizarin red S, and protease inhibitors were obtained from Sigma (St. Louis, Mo.). Fetal bovine serum was purchased from Atlanta Biologicals, and α-MEM was from Irvine Scientific (Santa Ana, Calif.). G418 was from Invitrogen. Radiochemicals were obtained from PerkinElmer Life Sciences. Culture and differentiation of low passage MC3T3-E1 cells by exposure to ascorbic acid and β-glycerol phosphate has been described previously (Beck, et al. (2001) *Cell Growth & Differ.* 12:61-83).

shRNA and Isolation of Stable BRM and BRG1 Knockdown Lines. The shRNA sequences were tested in a pSUPER vector (Brummelkamp, et al. (2002) *Science* 296:550-553). For BRM, two targeted constructs were generated using the RNAi Designer provided by Clontech. The 64-bp forward sequence for the first (BRM:seq1rnai) sequence was: 5'-gat ccc cgatccagaagctctccaaat tca aga gatttggagagcttctggatc ttt ttg gaa a-3' (SEQ ID NO:1; the 19-bp target sequence is underlined). The respective 19-bp sequence for the alternative BRM sequence (BRM:seq5rnai) was 5'-gtc ata agc ctg agg caa a-3' (SEQ ID NO:2). The respective 19-bp BRG1 target sequence was 5'-gcc tat gga gtc cat gca c-3' (SEQ ID NO:3) (adapted from Wang, et al. (2004) *J. Biol. Chem.* 279:46733-46741). The pSUPER-derived vectors containing the respective knockdown sequences were introduced into MC3T3-E1 cells by lipofection together with a selectable neo marker. G418-resistant clones were amplified and screened by western blot analysis for BRM or BRG1 expression. Aliquots of low passage depleted lines were frozen as stocks. A control line transfected with a scrambled non-targeting sequence has been described previously (Nagl, et al. (2006) *Cancer Res.* 66:1289-1293).

Alkaline Phosphatase Staining. Cell monolayers were rinsed in PBS (phosphate-buffered saline), fixed in 100% methanol, rinsed with PBS, and then overlaid with 1.5 ml of 0.15 mg/ml BCIP (5-bromo-4-chloro-3-indolyl phosphate) plus 0.3 mg/ml NBT (nitro blue tetrazolium; PROMEGA, Madison, Wis.) for 30 minutes and rinsed again with PBS three times.

Mineralization Assay. Cells were induced and plated as described herein. The monolayers were washed with PBS, covered with 0.1% alizarin red S for 10 minutes, and then rinsed with PBS three times and dried.

Northern Blot Analysis. Total cell RNA was prepared using TRIZOL reagent (Invitrogen) or TRI REAGENT (Sigma) according to manufacturer's recommendations. Twenty µg of RNA were loaded per lane and separated by electrophoresis through a 1% formaldehyde-agarose gel. The RNA was transferred to a HYBOND-N nylon membrane (Amersham Biosciences) and cross-linked by UV irradiation. $^{32}$P-labeled probes were prepared using a random primer labeling kit (Roche Applied Science). Five hundred µCi of [α-$^{32}$P]ATP was used per labeling reaction. Between successive probes, blots were stripped by treatment with boiling 0.1% SDS. The osteocalcin probe and plasmid pGB.GAPDH are known in the art (Beck, et al. (1998) *J. Cell. Biochem.* 68:269-280; Beck, et al. (2003) *Exp. Cell Res.* 288:288-300).

Immunoblot Analysis. Cells were washed and harvested in PBS and lysed in p300 lysis buffer (Yaciuk & Moran (1991) *Mol. Cell. Biol.* 11:5389-5397). Proteins were separated by polyacrylamide gel electrophoresis, transferred to IMMOBILON-P membrane (Millipore), and visualized using either Western Lighting chemiluminescence reagent Plus (PerkinElmer Life Sciences) or BCIP/NBT (Promega).

Real-Time PCR Assay. Real-time assays were performed with the RT$^2$ PROFILER PCR array: mouse osteogenesis (Super-Array, Frederick, Md.), according to the manufacturer's directions. The array contained primer sets for 84 osteogenesis-related genes and five housekeeping genes. The starting amount of RNA used was 1 µg. PCR was carried out on an ABI7500 cycler using the following parameters: 1 cycle for 10 minutes at 95° C. and 40 cycles for 15 seconds at 95° C., 1 minute at 60° C. Data were analyzed using the PCR Array Data Analysis Web Portal.

All quality control parameters (genomic DNA control, reverse transcription control, and positive PCR control) were within manufacturer's recommended limits in each assay. Results for each assay were normalized to the average of all five housekeeping genes. The parental cell population and the scrambled sequence line were each analyzed in duplicate, and the averages were compared. The 10 genes that differed more than 4-fold between these two controls were excluded from further consideration. Each of the three independent BRM knockdown lines (GG5, ZD1, and ZD17) was analyzed in duplicate, and the average of the six runs was compared with the average of the parental and scrambled cells to obtain the fold change. Likewise, the two BRG1 knockdown lines (D16 and B19) were analyzed in duplicate and again compared with the parental and scrambled cells. The results of this analysis are listed in Table 1. In accordance with recommended thresholds, a gene expression change is reported in Table 1 if it was greater than 4-fold and the t test p value was less than 0.05.

TABLE 1

| | | Fold Up- or Down-Regulation | |
|---|---|---|---|
| Gene Name | Common Name of Gene Product | BRM-Deficient Cells (p value BRM) | BRG1-Deficient Cells (p value BRG1) |
| Akp2 | Alkaline phosphatase, liver/bone/kidney | 4.38 (0.0415) | −11.85 (0.0038) |
| Bmp4 | Bone morphogenetic protein 4 | 1.82 (0.3188) | −22.93 (0.0001) |
| Bmpr1b | Bone morphogenetic protein receptor, type 1B | 4.03 (0.0020) | 9.26 (0.0051) |
| Cd36 | CD36 antigen | 6.03 (0.000) | Undet[3] (0.0116) |
| Col11a1 | Collagen, Type XI, alpha 1 | 8.23 (0.0003) | −5.83 (0.0001) |
| Col12a1 | Collagen, Type XII, alpha 1 | −1.72 (0.0001) | −5.84 (0.0000) |
| Col1a1 | Collagen, Type I, alpha 1 | −4.49 (0.0010) | −5.12 (0.0000) |
| Col1a2 | Collagen, Type I, alpha 2 | −1.26 (0.1035) | −4.72 (0.0000) |
| Col4a1 | Collagen, Type IV, alpha 1 | −2.19 (0.0041) | −25.51 (0.0430) |
| Col4a2 | Collagen, Type IV, alpha 2 | −1.31 (0.3887) | −10.53 (0.0000) |
| Col5a1 | Collagen, Type V, alpha 1 | −4.30 (0.0004) | −5.13 (0.0000) |
| Dmp1 | Dentin matrix protein 1 | 18.27 (0.0001) | 43.01 (0.0000) |
| Fgfr2 | Fibroblast growth factor receptor 2 | 1.63 (0.2228) | −134.53 (0.0148) |
| Flt1 | Fms-related tyrosine kinase 1 (VEGF receptor-1) | −3.05 (0.0082) | −9.92 (0.0001) |
| Icam1 | Intracellular adhesion molecule 1 precursor (CD54 Ag) | 3.30 (0.0118) | 5.40 (0.0052) |
| Itgam | Integrin, alpha M (CD11b antigen) | 7.79 (0.0077) | 23.65 (0.0000) |
| Mmp10 | Matrix metalloproteinase 10 (Stromelysin 2) | 4.68 (0.0266) | 3.21 (0.0867) |
| Msx1 | Homeobox protein MSX-1 | 4.54 (0.0036) | −14.69 (0.0559) |
| Phex | Phosphate regulating endopeptidase homolog | 16.07 (0.0003) | 13.41 (0.0000) |
| Tuft1 | Tuftelin 1 | 5.25 (0.0173) | 2.36 (0.0157) |

[1] Fold change in gene expression levels was determined as described herein. Positive changes are underlined; negative changes are in italics.
[2] Undet product was not detected.

Of the 84 genes on the array, 10 (Col10a1, Csf2, Fn1, Igf1, Mmp9, Serpinh1, Smad2, Smad3, Sox9, and Tnf) differed more than 4-fold between the scrambled cell line and the parental population and were therefore regarded as too variable for analysis in the knockdown lines. A further 54 were unaffected by either knockdown. They were: Ahsg, Ambn, Anxa5, Bgn, Bmp1, Bmp2, Bmp3, Bmp5, Bmp6, Bmpr1a, Cdh11, Col12a1, Col14a1, Col3a1, Col6a1, Col6a2, Col7a1, Comp, Csf3, Ctsk, Egf, Enam, Fgf1, Fgf2, Fgf3, Fgfr1, Gdf10, Igf1r, Itga2, Itga2b, Itga3, Itgav, Itgb1, Mmp2, Mmp8, Nfkb, Pdgfa, Runx2, Scarb1, Smad1, Smad4, Sost, Tfip11, Tgfb1, Tgfb2, Tgfb3, Tgfbr1, Tgfbr2, Tgfbr3, Twist1, Vcam, Vdr, Vegfa, and egfb.

ChIP Assays. Chromatin immunoprecipitation (ChIP) assays were performed with the EZ CHIP system (Upstate Cell Signaling Solutions, Lake Placid, N.Y.), according to the manufacturer's directions, modified to include preclearing of lysates with 60 μl of a 50% slurry of protein G/salmon sperm DNA for 1 hour at 4° C., and again performed overnight. Negative controls included either IgG or the viral-specific monoclonal antibody 419. Primer sequences are listed in Table 2. PCR conditions were 40 cycles at for 30 seconds at 95° C., 30 seconds at 72° C., and 30 seconds at 60° C.

TABLE 2

| Promoter (GENBANK Accession #) | | Primer Sequence | SEQ ID NO: |
|---|---|---|---|
| Akp2 (NM_007431) | Forward Reverse | ggctgggacagacagaatgt ctttgtccctcgatggttgt | 4 5 |
| Col11a1 (NM_007729) | Forward Reverse | gcaaggtttttggagatgga gcactttgggaatgaaagga | 6 7 |
| Col5a1 (NM_015734) | Forward Reverse | tgtgagttgttgggccacta tctggctgaattgcaagttg | 8 9 |
| Itgam (NM_008401) | Forward Reverse | acaggtggtcagcgcttagt atgtgggtactgggagcaag | 10 11 |
| Mmp10 (NM_019471) | Forward Reverse | caggtgtggtggcctaaagt aactgcctgaggtgctgagt | 12 13 |
| Msx1 (NM_010835) | Forward Reverse | acttgttcccgtacccacag ttctgtcccctttccctctt | 14 15 |
| Phex (NM_011077) | Forward Reverse | cctgagtttggggtgaaatg tgacaccagacctcagcaag | 16 17 |
| Tuft1 (NM_011656) | Forward Reverse | agcctacaggctggcttaca ctaccgtgctatggacgat | 18 19 |
| Osteocalcin (NM_001032298) | Forward Reverse | ctgaactgggcaaatgaggaca aggggatgctgccaggactaat | 20 21 |

Re-ChIP Assays. Re-ChIP assays were performed with the Active Motif RE-CHIP-IT system (Active Motif, Carlsbad, Calif.), according to the manufacturer's directions. The assay was modified to include overnight incubations of the antibodies at 4° C., for both the first and the second chromatin IP. Primer sequences for osteocalcin are listed in Table 2. PCR conditions are same as described herein.

Antibodies. Antibodies of the following specificities were obtained from commercial sources: PEB2αA/RUNX2 (s-19 sc12488), BRM (N-19, sc-6450), BRG1 (H-88 sc-10768), and HSC70 (B-6, sc-7298) (Santa Cruz Biotechnology, Inc., Santa Cruz, Calif.); SNF5/INI1 (612110, BD Biosciences); anti-trimethyl-histone H3 (Lys 4) (catalog number 04-745, Millipore); and HDAC1 (catalog number 2062, Cell Signaling). Monoclonal antibodies specific for p270/ARID1A (PSG3), ARID1B (KMN1), and SV40 T antigen (419) are known in the art (Nagl, et al. (2007) supra; Wang, et al. (2004) Biochem. J. 383:319-325).

EXAMPLE 2

Phenotypic Analysis of BRG1 and BRM Knockdown Lines

DNA sequences encoding shRNA molecules complementary to either Brg1 or Brm were introduced from a plasmid vector by stable integration into low passage MC3T3-E1 cells. In each transfection, colonies appeared at similar frequencies and showed essentially the same doubling time in normal growth medium as a vector-only control. The resultant lines were screened for the ability to respond to an ascorbic acid signal by induction of two key indicators of osteoblast differentiation: increased alkaline phosphatase activity and formation of a mineralized matrix. Alkaline phosphatase is among the earliest markers of osteoblast differentiation. The enzyme is exported to the osteoblast cell surface, where its activity can be visualized in a sensitive in situ assay scored by color development. The BRG1-depleted line showed severely impaired induction of alkaline phosphatase activity.

Unexpectedly, the BRM-depleted line showed an enhanced level of alkaline phosphatase activity even in non-induced cells (day 0) and an enhanced induction in response to the differentiation signal.

The same patterns were seen when the cells were tested for mineralization activity. Formation of calcium-containing mineralization products in the cell matrix can be detected by staining with Alizarin Red S. In this assay, the BRG1-depleted line again behaved as expected, showing virtually no mineralization. In addition, unexpectedly again, but consistent with the alkaline phosphatase induction pattern, the BRM-depleted cells showed accelerated progression to the mineralization phenotype beginning on day 7 post-induction compared to day 21 for Parental cell lines. A control cell line (J6) derived from transfection with a non-targeting sequence behaved like the parental cells.

Because this pattern was so contrary to expectations, additional BRM-depleted lines were constructed using a second, independent, shRNA sequence. Two separate clones (ZD1 and ZH17) were isolated. The pattern of all three BRM-depleted lines showed the same phenotype. In each line, there was a constitutively enhanced level of alkaline phosphatase activity (day 0), accelerated induction of alkaline phosphatase activity, and accelerated progression to the mineralization phenotype. Rather than augmenting BRG1-dependent progression to terminal differentiation, the BRM-containing subset of SWI/SNF complexes participates in an opposing pathway, restraining differentiation.

Western blot analysis with antibodies specific for BRM and BRG1, respectively, indicate that depletion of one ATPase subunit does not have a major effect on expression of the other. It is also known from established tumor cell lines that deficiency of BRG1 or BRM, or both, does not otherwise disrupt assembly of the SWI/SNF complex (Wang, et al. (1996) *EMBO J.* 15:5370-5382).

EXAMPLE 3

Osteocalcin is Constitutively Expressed in BRM-Depleted Cells

The best studied marker of late stage differentiation in osteoblasts is the mineralized matrix component osteocalcin. The osteocalcin gene (Bglap2) is a well-established model for induction of tissue-specific gene expression whose activation has been shown to be dependent on SWI/SNF complex activity in a differentiating rat osteosarcoma cell line (Villagra, et al. (2006) *J. Biol. Chem.* 281:22695-22706; Montecino, et al. (2007) *Biochem. Cell Biol.* 85:419-425). To probe the molecular events underlying the phenotypes of the knockdown lines, osteocalcin expression was assessed quantitatively by northern blot analysis. Normally, osteocalcin expression is barely detectable in non-induced cells. After induction of differentiation, expression increases dramatically in parallel with mineral deposition. Northern blot analysis showed the typical pattern of osteocalcin (OSC) induction in parental cells as compared with expression in BRM and BRG1 knockdown lines. The BRG1-depleted cells showed greatly impaired induction of osteocalcin, correlating with the severe defect in mineralization phenotype. In contrast, BRM-depleted cells showed strikingly high constitutive expression of osteocalcin and rapid induction to higher levels, concordant with the accelerated mineralization phenotype. Results averaged from three independent experiments are shown quantitatively in FIG. 1.

EXAMPLE 4

Real-time PCR Array Analysis of Osteogenesis-Associated Gene Expression

The deregulation of the osteocalcin gene indicated that BRM-depleted cells had lost a major promoter repression function. To gauge the extent of genes affected by BRM depletion, an array of 84 osteogenesis-associated genes was analyzed in the osteoblast precursors by quantitative real-time reverse transcription-PCR (QPCR). Each of the three independent BRM knockdown lines (GG5, ZD1, ZD17) was analyzed in duplicate, and the average of the six runs was compared with the average of duplicate runs performed on both parental cells and the J6 control line to obtain the fold change. Taking the recommended 4-fold difference as the cut-off point, 12 genes scored as affected by BRM depletion in this assay; 10 were up-regulated, and two were down-regulated (Table 1). (Osteocalcin was not present on the array.)

Among the genes constitutively up-regulated in BRM-depleted cells was Akp2, encoding alkaline phosphatase, a major osteoblast differentiation marker whose increase was also apparent at the level of enzyme activity. The remainder of the list encompassed genes from multiple classes, including those encoding hematopoietic cell-associated antigen CD11b (Itgam) and the widely expressed CD36 antigen, both of which have been observed in differentiating osteoblasts (Reyes-Botella, et al. (2002) *Cell Physiol. Biochem.* 12:359-364; Brodeur, et al. (2008) *J. Bone Miner Res.* 23:326-337). Genes encoding various extracellular matrix components (DMP1, collagen 11, and tuftelin) were activated. In addition, expression of the enzyme-encoding genes Phex and Mmp10 was increased. These enzymes, like alkaline phosphatase, participate in phosphate and matrix metabolism. The list also included genes encoding one of the receptors for the bone morphogenic proteins (Bmpr1b), as well as the osteogenic transcription factor MSX1.

Not every osteoblast marker on the array was constitutively activated in BRM-depleted cells, nor would they be predicted to be as the BRM-depleted cells did not mineralize spontaneously, and only a minority of promoters is thought to be targets of regulation mediated by the SWI/SNF complexes. The two down-regulated genes in the BRM-deficient cells both encode additional members of the large collagen gene family. Down-regulation of these two genes diverged from the general pattern, but the overall profile was clearly consistent with a central role for BRM complexes in restraining precocious osteoblast differentiation.

The effect of BRG1 depletion was analyzed as well. This analysis indicated that multiple genes whose expression is characteristic of osteoblast commitment were down-regulated in BRG1-depleted cells. A comparison of the effects of BRG1 versus BRM depletion (Table 1) highlights the largely antagonistic nature of their effects, consistent with the concept that the two ATPases are specificity determinants of complexes with generally opposing roles in osteogenesis.

EXAMPLE 5

Identification of Direct Targets of BRM-Specific Complexes

The gene array results identified a minimum of 10 osteogenesis markers in addition to osteocalcin that were coordinately derepressed as a consequence of BRM deficiency. This did not, however, indicate whether the promoters of these genes were direct targets of BRM complexes. To address this, a panel of BRM-affected genes whose promoter sequences were readily identifiable was probed by ChIP analysis in non-induced cells. At least six genes were revealed in this manner to be direct targets of BRM complexes: Akp2, Col11a1, Mmp10, Msx1, Phex, and osteocalcin. In addition, BRM was weakly detectable on the Itgam promoter. In each of these cases, the promoter occupation pattern was consistent with a role for BRM complexes in promoter repression. BRM was not detected on the Col5a1 or Tuft1 promoters, implying that BRM affects these genes only indirectly. This was of particular note for the divergently regulated Col5a1, but negative results remained inconclusive. In most cases where one of the ATPases was identified in association with the promoter, the occupation was either/or with respect to BRM versus BRG1. However, BRG1 was readily detected along with BRM on the Phex and osteocalcin promoters. Phex was one of the minority cases seen in Table 1 in which BRG1 also appeared to contribute a repressor role, so this was consistent with the ChIP results. In contrast, BRG1 was a required activator of osteocalcin, and the apparent presence of both ATPases simultaneously on this promoter implied a more complex mechanism of regulation of this key gene product. The osteocalcin promoter is by far the best characterized of the identified BRM-targeted promoters and was subjected to further detailed analysis. First, a serial ChIP assay was performed to determine whether the two ATPases actually do associate with this promoter simultaneously. The re-ChIP (ChIP 2) analysis confirmed that BRG1 was present on the BRM-precipitated promoter DNA, and conversely, that BRM was present on the BRG1-precipitated promoter DNA.

EXAMPLE 6

BRM Complexes Override BRG1-dependent Activation of the Osteocalcin Promoter

The simplest mechanisms by which BRM-specific complexes might repress expression from a particular promoter would be by preventing association of a required activator or co-activator or by facilitating association of a required repressor or co-repressor. The results demonstrated that BRM complexes did not necessarily simply compete with BRG1 complexes for promoter association. Prior analysis of the osteocalcin promoter had identified certain other key factors that were considered here. RUNX2/CBFA1 is a major tissue-specific transcriptional activator controlling lineage commitment in osteoblasts (Yang & Karsenty (2002) *Trends Mol. Med.* 8:340-345) and is known to be associated with the osteocalcin promoter prior to activation (Villagra, et al. (2006) supra; Schroeder, et al. (2004) *J. Biol. Chem.* 279: 41998-42007; Lee, et al. (2006) *J. Bone Miner Res.* 21:921-933). In contrast to activation, transcriptional repression typically involves associated histone deacetylase (HDAC) activity. HDAC1 appears to be a key regulator for osteoblast differentiation and has been identified in association with the osteocalcin promoter specifically in the predifferentiation (i.e. repressed) state in primary bone marrow cells (Lee, et al. (2006) supra).

Runx2 was included in the QPCR array, and notably, its expression in the non-induced cells was unaffected by depletion of either ATPase. Prior to differentiation, BRM, BRG1, RUNX2, and HDAC1 could all be seen in association with the promoter in parental cells. Association of RUNX2 was unaffected by BRM depletion in the BRM.GG5 cell line, whereas association of HDAC1 was lost in BRM.GG5 cells. Analysis of the BRG1.D16 line showed that BRG1 complexes, although present on the repressed promoter, were not linked with association of HDAC1. The association patterns are represented schematically in FIG. 2. These results combined with the biological phenotype indicate that the promoter is poised for expression in non-induced cells but that expression functions are overridden by the presence of BRM-containing complexes and their HDAC1 affiliate. Depletion of BRM essentially converts the association profile of the key indicators from the pattern characteristic of the repressed promoter in parental cells to the pattern characteristic of the active promoter. The promoter in the BRM.GG5 line at day 0 was almost as active as the parental promoter at day 21 of differentiation.

EXAMPLE 7

ARID Family Subunits Associate Differentially with the Osteocalcin Promoter

Figure 2:
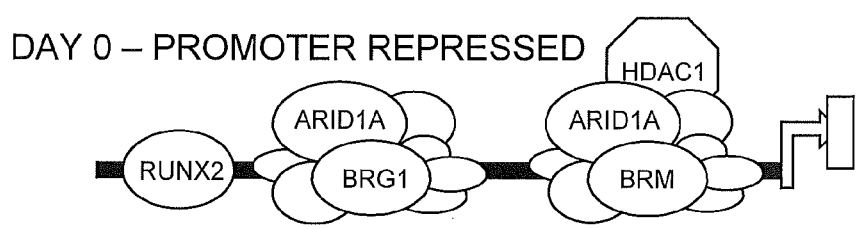
FIG. 2 is a schematic representation of the dynamics of complex association on the proximal osteocalcin promoter. The association of key factors at the osteocalcin promoter at major points during differentiation in normal cells as determined by ChIP analysis is represented schematically. The unlabeled circles represent the invariable subunits of the SWI/SNF complex. The relative positions of the complexes are indicated arbitrarily. HDAC1 is drawn in association with the BRM complex prior to induction to indicate its specific dependence on BRM association. Dissociation of HDAC1 precedes BRM complex dissociation, and binding of an ARID1B-containing complex precedes complete dissociation of ARID1A-containing complexes, indicating the existence of a transition configuration on a partially activated promoter at around day 7.
Figure 2:
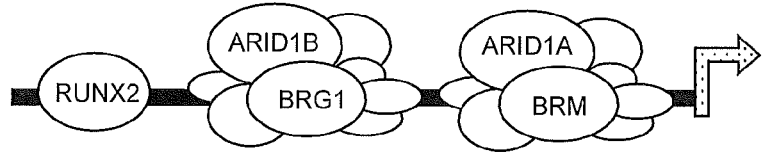
Figure 2:
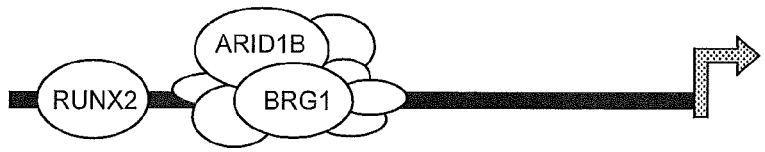

It has been reported that the SWI/SNF subunits, ARID1A and ARID1B, are specificity determinants of complexes that play repressing versus activating roles, respectively, on pro-proliferative genes (Nagl, et al. (2007) supra). These are the only subunits other than the ATPases known to exist as a mutually exclusive pair in most cells. Examination of the association pattern of the ARID family subunits with the osteocalcin promoter showed ARID1A present only on the repressed promoter and ARID1B present only when the promoter was active. ARID1A association was not dependent on either ATPase individually, so this subunit was likely associated with both complexes on the repressed promoter. Because only ARID1B was on the active promoter, it appeared that the BRG1 complex changed from an ARID1A-containing configuration on the repressed promoter to an ARID1B-containing configuration on the active promoter (FIG. 2). As a further control, the presence of the INI1/SNF5 subunit was also probed. INI1/SNF5 was present in all known subsets of the complex. Its association profile was consistent with this and with a general finding that the presence of an ATPase subunit was required for promoter association of the complex as a whole.

Although the ARID family subunits help to distinguish activator versus repressor complexes, their role was apparently not essential on the osteocalcin promoter as the ARID1A and ARID1B knockdown lines did not show major differences in mineralization phenotypes. This was consistent with the ChIP results indicating that the BRG1 complex does not need to switch to an ARID1B subunit to effect constitutive activation of osteocalcin in BRM-depleted cells. However, a complex specifically containing BRG1 itself is clearly required for activation. The four different combinations of ARID subunit and ATPase (Wang, et al. (2004) supra; Lee, et al. (2006) supra) help explain how each of the subunits can be identified on both active and repressed promoters, although their respective roles are not random. The significance of the alternative subunits is only beginning to be addressed, but evidence indicates a general pattern in which BRM+ARID1A complexes are linked most closely with repression and BRG1+ARID1B complexes are linked most closely with activation, whereas the other possible combinations, BRM+ARID1B and BRG1+ARID1A, are more variable in their activities.

EXAMPLE 8

Disassociation of BRM from the Osteocalcin Promoter Correlates Temporally with Up-regulation of Osteocalcin Expression To obtain a more dynamic picture of SWI/SNF-mediated regulation of the osteocalcin promoter, the association of key factors was probed at major intermediate time points. The results showed that BRM was still present at day 7 but dissociated by day 14. This correlated well with the pattern of osteocalcin induction, which rose rapidly between days 14 and 21. The results revealed further that dissociation of HDAC1 preceded dissociation of BRM and that association of ARID1B preceded complete dissociation of ARID1A. The promoter association dynamics implied the existence of a transition point at about day seven when the promoter was undergoing initial stages of activation (FIG. 2, schematic), which correlated with the initial level of activation seen at day 7 in northern blots. Presumably, following this transition period, other chromatin events occur that lead to full activation. One important event characteristic of activated promoters and associated with increased histone acetylation is trimethylation at histone H3 lysine 4 (H3K4) (Nightingale, et al. (2007) *J. Biol. Chem.* 282:4408-4416). This modification increased on the osteocalcin promoter at later times (days 14 and 21) coordinately with dissociation of the BRM complexes.

What is claimed is:

1. A method for promoting the differentiation of osteoblast bone forming cells to a mineralization phenotype comprising contacting osteoblast bone forming cells or progenitor cells thereof with an effective amount of an antisense molecule, ribozyme, RNAi or triple helix molecule that decreases the expression of Brahma so that the differentiation of osteoblast bone forming cells or progenitor cells thereof to a mineralization phenotype is promoted, wherein the antisense molecule, ribozyme, RNAi or triple helix molecule is targeted to SEQ ID NO:1, SEQ ID NO:2, or SEQ ID NO:3.

2. A method for increasing bone mass, bone healing or bone formation comprising administering to a subject in need of osteoinduction an effective amount of an antisense molecule, ribozyme, RNAi or triple helix molecule that decreases the expression of Brahma thereby increasing bone mass, bone healing or bone formation in the subject, wherein the antisense molecule, ribozyme, RNAi or triple helix molecule is targeted to SEQ ID NO:1, SEQ ID NO:2, or SEQ ID NO:3.

3. The method of claim 2, wherein the subject has a non-union fracture.

4. The method of claim 2, wherein the subject has osteopenia or osteoporosis.

5. The method of claim 2, wherein the subject has osteosarcoma.

6. The method of claim 2, wherein the subject has a bone graft.

7. The method of claim 2, wherein the subject has a bone fusion or arthrodesis procedure.

8. The method of claim 2, wherein the subject has a skeletal defect or deficiency.

9. The method of claim 2, wherein the subject has osteoarthritis.

10. The method of claim 2, wherein the subject has a periodontal disease or defect.

11. The method of claim 2, wherein the subject has an osteolytic bone disease.

12. The method of claim 2, wherein the subject has a post-orthopedic implantation or post-dental implantation.

* * * * *